United States Patent [19]

Sie et al.

[11] Patent Number: 4,888,361
[45] Date of Patent: Dec. 19, 1989

[54] PROCESS FOR THE PRODUCTION OF METHANOL AND CATALYST COMPOSITION FOR SAID PROCESS

[75] Inventors: Swan T. Sie; Eit Drent; Willem W. Jager, all of Amsterdam, Netherlands

[73] Assignee: Shell Oil Company, Houston, Tex.

[21] Appl. No.: 231,924

[22] Filed: Jan. 17, 1989

[30] Foreign Application Priority Data

Sep. 4, 1987 [EP] European Pat. Off. ........ 87201680.3

[51] Int. Cl.$^4$ .............................................. C07C 27/06
[52] U.S. Cl. .................................. 518/700; 518/885; 518/717
[58] Field of Search ............................. 518/700, 717

[56] References Cited

U.S. PATENT DOCUMENTS 4,614,749 9/1986 Sapienza et al. .................... 518/700
4,619,946 10/1986 Sapienza et al. .................... 518/700

FOREIGN PATENT DOCUMENTS 56-196634 12/1981 Japan .

Primary Examiner—Howard T. Mars

[57] ABSTRACT

A process for the production of methanol comprising contacting a gaseous mixture of carbon monoxide and hydrogen with a catalytic system, obtainable by combination of:

component (a): a salt containing a cation of an element of Group VIII of the Periodic Table of the Elements, component (b): an alcohol, and component (c): an alcoholate derived from an alkali metal or from an alkaline earth metal, and activation the combined components, and a catalyst system to be used in this process.

17 Claims, 2 Drawing Sheets $T_2 > T_1$

PROCESS FOR THE PRODUCTION OF METHANOL AND CATALYST COMPOSITION FOR SAID PROCESS

FIELD OF THE INVENTION

The invention relates to a process for the production of methanol and a catalyst composition for said process.

BACKGROUND OF THE INVENTION

A process for the production of methanol is described in U.S. Pat. No. 4,619,946 issued Oct. 28, 1986, comprising reacting at relatively low temperature carbon monoxide with hydrogen in the presence of a catalytic system derived from sodium hydride, sodium alcoholate and acetate of nickel, palladium or cobalt. The alcoholate applied is preferably a lower alkanolate having 1–6 carbon atoms and more preferably a tert-alkanolate, while as metal salt nickel acetate is preferably used.

The catalyst is subjected to a conditioning or activating step for a prolonged time with a gaseous mixture comprising carbon monoxide and hydrogen at such an elevated temperature and elevated pressure that a substantial amount of carbon monoxide and hydrogen is consumed for this conditioning.

Also in U.S. Pat. No. 4,614,749 issued Sept. 30, 1986, a process is disclosed for the production of methanol at relatively low temperature by reaction of carbon monoxide with hydrogen in the presence of a slurry catalyst system resulting from combination of a complex reducing agent comprising sodium hydride-alcohol and an acetate of nickel, palladium or cobalt, and a carbonyl complex of one of the group VI metals.

The alcohol to be applied is preferably selected from lower alkanols, having from 1 to 6 carbon atoms and more preferably tertiary amyl alcohol.

Another process for the production of methanol is described in published Japanese patent application No. 56-169,634. This process comprises reacting carbon monoxide and hydrogen in the presence of a catalyst comprising a nickel compound and a metal alkoxide, in the lquid phase at temperatures of 200° C. or lower. More preferably an alkali metal alkoxide might be used. The catalyst to be used for this process may be prepared by mixing a nickel compound with an alkali metal alkoxide, while it is preferable to use an organic diluent which is liquid under the preparation and use conditions of the catalyst system.

More particularly the teachings of this Japanese patent application instruct a person skilled in the art, that a high reaction rate may be reached by preparing the catalyst system with the use of a substantially alcohol free organic diluent and that it is desirable that an alcohol be not present in the reaction system at the commencement of the reaction.

Although improvements in the preformances of the catalyst systems as described hereinbefore, could be reached as compared to those used in the conventional methanol manufacturing processes, requiring severe conditions, the still growing demand for cheaper methanol as starting material for a still increasing area of chemical syntheses evoked continuing research efforts for a further improved methanol manufacturing process as compared to the currently operated high pressure processes.

With the term improved methanol manufacturing process is meant a process utilizing the catalyst having enhanced activity, retaining its activity for a long time under economically more attractive operating conditions.

An object of the present invention is therefore to provide such an improved manufacturing process for methanol. Another object of the present invention is to provide an improved catalyst system therefor.

SUMMARY OF THE INVENTION

The invention relates to a process for the production of methanol by reaction of carbon monoxide with hydrogen in the presence of a catalytic system in the liquid phase derived from at least a salt containing a cation of an element of Group VIII of the Periodic Table of the Elements an alcohol and an alcoholate. Specifically, the process comprises contacting a gaseous mixture of carbon monoxide and hydrogen with a catalytic system, obtainable by combining the following components:

component (a): a salt containing a cation of an element of Group VIII of the Periodic Table of the Elements, component (b): an alcohol, and component (c): an alcoholate derived from an alkali metal or from an alkaline earth metal, and activating the combined components.

DESCRIPTION OF THE PREFERRED EMBODIMENTS

Figure 1:
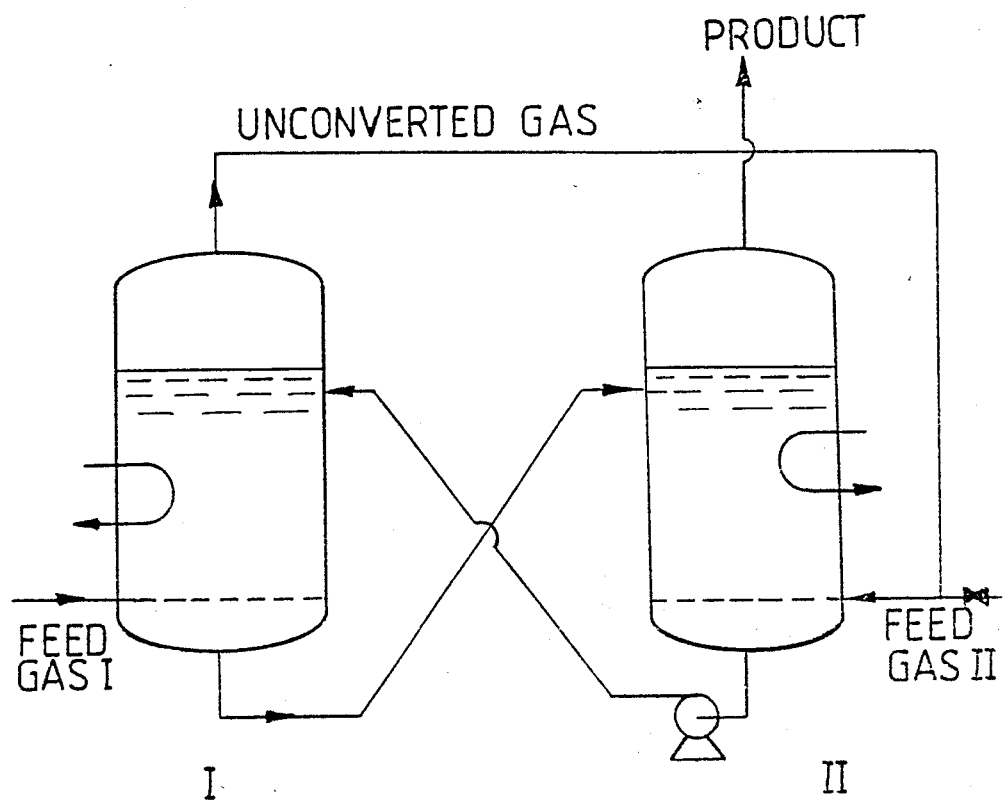
FIG. 1 illustrates a preferred process embodiment wherein feed gas to a first (carbonylation) reactor has a lower $H_2/CO$ ratio than the feed gas to a second (hydrogenation) reactor.

The elements of group VIII of the Periodic Table of the Elements that may be used in the salt component (a) may be selected from iron, cobalt, nickel, ruthenium, rhodium, palladium, osmium, iridium and platinum. More preferred are nickel, palladium and cobalt salts and most preferably nickel salts are used.

The anion of the salt in component (a) may be derived from a great variety of acids. It is preferred that the salt in component (a) is a salt of a carboxylic acid or sulphonic acid. Among these acids preference is given to alkanoic acids having 1-10 carbon atoms in the chain or to paratoluene sulphonic acid. More preferably formic acid, acetic acid and oxalic acid or p-toluene sulphonic acid are used. Component (a) is most preferably nickel formate, nickel acetate, nickel oxalate or nickel tosylate.

Examples of carboxylic acids from which component (a) also may be derived are dicarboxylic acids such as malonic acid, dimethylmalonic acid, succinic acid, glutaric acid, adipic acid, pimelic acid, suberic acid, azelaic acid, phthalic acid, isophthalic acid and terephthalic acid. The carboxylic acids from which component (a) may be derived may contain substituents, for example alkoxy groups, particularly those having not more than five carbon atoms, hydroxy groups, cyano groups and fluorine, chlorine, bromine and iodine atoms. Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5- dichlorobenzoic acid, 3,5-dibromobenzoic acid, cyanoacetic acid, monofluroacetic acid, difluoroacetic acid, trifluoroacetic acid and trichloroacetic acid.

Other examples of suitable acids from which component (a) may be derived are propanoic acid, butanoic acid, 2-methylpropanoic acid, pentanoic acid, 3-methylbutanoic acid, 2,2-dimethylpropanoic acid, hexanoic acid, heptanoic acid and octanoic acid, hydrochloric acid, sulphuric acid, nitric acid and phosphoric acid.

A mixture of the salts in question may be used in component (a), for example of a formate and an oxalate, of a formate and an acetate, of acetate and an oxalate.

The salts in component (a) may contain crystal water, but are preferably free therefrom.

The alcohol of component (b) may be cycloaliphatic or aliphatic but is preferably aliphatic. Preference is given to alkanols, in particular to those having in the range of from 1 to 20 carbon atoms per molecule. Among the latter alkanols those having in the range of from 4 to 20 carbon atoms per molecule are preferred. Examples of suitable alkanols are tert-butyl alcohol, tert-amyl alcohol, isoamylalcohol, hexanol, heptanol, but higher alkanols having in the range of from 8 to 20 carbon atoms per molecule may also be used. Tert-butyl alcohol and tert-amyl alcohol are particularly preferred.

Dihydric alcohols may also be used, for example ethylene glycol, propylene glycol, 1,3-dihydroxypropane, 1,2-butanediol, 1,3-butanediol, 1,4-butanediol, 2,3-butanediol or 1,2-pentanediol. Component (b) may also be glycerol.

Component (b) also may be a mixture of alcohols, for example of tert-butyl alcohol and tert-amyl alcohol or isoamyl alcohol and 1,4-butanediol.

The alcoholate of component (c) is preferably a sodium alcoholate or a potassium alcoholate. Among the alcoholates preference is given to alkoxides, particularly to those having in the range of from 1 to 20 carbon atoms per molecule, such as sodium methoxide, sodium ethoxide, sodium propoxide, sodium butoxide, sodium isobutoxide, sodium tert-pentoxide and potassium 2-methyldodec-2-oxide. Most preferred is potassium tert.-butoxide.

An activation of the catalyst system to be used in the present process can be reached by a great variety of methods, as will be known to the person skilled in the art.

According to a preferred embodiment, which has appeared to give rise to attractive results, activation may be reached by keeping the mixed components (a) and (b) and diluent if used, under an atmosphere of nitrogen or any other suitable inert gas during 0.3 to 1 hour at a temperature in the range of from 20°–60° C. and more preferably 35°–50° C.

After this activation, additional amounts of alcohol and alcoholate are added to complete the reaction mixture to which hydrogen/carbon monoxide gas can be added.

The process according to the present invention may be carried out at a temperature and a pressure which are not critical and may vary within wide ranges. Preferably, a temperature in the range of from 30° C. to 120° C. and a pressure in the range of from 5 to 100 bar are used.

The process according to the present invention may be carried out with an organic diluent in which the catalytic system is dissolved or is suspended. Suitably, a weight ratio of organic diluent to component (a) in the range of from 0.1 to 5000 is used, but this weight ratio may be lower than 0.1 or higher than 5000.

The reaction may be carried out in additional inert diluent or the starting alcohol (component b) may serve as reaction medium.

Examples of suitable diluents are ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; sulphones, such as diisopropyl sulphone, tetrahydrothiophene 1,1-dioxide (also referred to as "sulfolane"), 2-methyl-4-butylsulfolane and 3-methylsulfolane. Mixture of two or more solvents may be used. Very good results have been obtained with ethers and the use of diglyme is most preferred. The process may be carried out using a molar ratio of component (a) to component (b) which is not critical and may vary within wide ranges, preferably in the range of from 1:0.2 to 1:20 and more preferably of from 1:3 to 1:8.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably in the range of from 1:0.2 to 1:20. The carbon monoxide and hydrogen may preferably be obtained by partial oxidation of hydrocarbons, for example of natural gas with air or coal gasification, resulting in carbon monoxide-hydrogen mixtures containing nitrogen.

It will be appreciated by persons skilled in the art that the attractive results obtained according to the process of the present invention could certainly not be expected by them on account of the before mentioned prior art literature and that the teachings of many of them could only led away them from the present process.

The methanol produced according to the invention forms another feature of the invention. It may be used for a variety of purposes, for example for the manufacture of synthetic gasoline, as a fuel component and for the production of methyl tert-butyl ether.

The process according to the present invention may be carried out batchwise, semi-continuously or continuously.

It is preferred to remove methanol in the gaseous phase from the reaction mixture. This can be done by stripping the reaction mixture with carbon monoxide and hydrogen. Methanol can be recovered from the used stripping gas in any suitable manner for example by condensation.

It will be appreciated that another object of the present invention is formed by the catalyst system in the process as described hereinbefore and which may be obtained by combining the following components:
component (a): a salt containing a cation of an element of Group VIII of the Periodic Table of the Elements,
component (b): an alcohol, and
component (c): an alcoholate derived from an alkali metal or from an alkaline earth metal.

It will be appreciated that another object of the invention is formed by the before identified catalyst system, mixed with one or more inert diluents and or carbon monoxide and hydrogen under an operational pressure suitable for the process of the invention, or lower.

It will be appreciated that according to a more preferred embodiment of the process of the present invention, it may be carried out as a two step process in at least two separated reactor zones, in which two different synthesis gas streams are introduced, containing excess carbon monoxide and excess hydrogen respectively ($H_2/CO$ ratio varying from 0.5 to 1.9 and more preferably 1.0–1.8 and $H_2/CO$ ratio varying from 2.5 to 4.5 and more preferably from 2.9 to 3.5) compared to the stoichiometric consumption ratio ($H_2/CO=2$).

In one of the zones a formate ester is formed (carbonylation step) e.g. methyl formate in the liquid phase using the catalyst system of the present invention in a low temperature process and using a feed gas, which is relatively rich in carbon monoxide, while in the other reaction zone this formate is hydrogenated in the liquid phase using the same catalyst composition and using a feed gas, which is relatively rich in hydrogen. The catalyst solution or slurry is circulated between the two reaction vessels.

In case a single synthesis gas stream is to be converted to methanol, a synthesis gas stream of higher $H_2/CO$ ratio is obtained by partial conversion of the first mentioned stream to form mainly the formate ester. The unconverted, hydrogen enriched residual gas stream from the first zone is used to hydrogenate this formate ester in the second zone.

According to a more preferred embodiment these two feed streams are derived from natural gas, which is converted by partial oxidation to synthesis gas, relatively rich in carbon monoxide, and by steam reforming to a gas relatively rich in hydrogen.

Although it might initially seem advantageously to carry out the two consecutive reaction steps, i.e.
(a) reaction of a carbon monoxide containing gas with an alcoholate to form a formate ester, e.g. methyl formate from alkali methanolate,
(b) hydrogenation/hydrogenolysis of the formate ester to form methanol and the alcohol from the original alcoholate (preferably also methanol),
in a single reactor being the most simple and straight forward way, the following negative features of such single step process may be appreciated:
(1) Formation of formate is a rapid reaction, but is limited by thermodynamic equilibrium, while hydrogenation of formate on the other hand is only limited by kinetics. Although the equilibrium limitation of alcohol carbonylation was found to be lifted by consecutive removal of formate, the steady state formate concentration has appeared to be relatively low since the conditions are governed to a large extent by the requirements of the second step.
(2) When a stoichiometric hydrogen/carbon monoxide synthesis gas mixture is converted at high methanol yield, the methanol concentration in the liquid catalyst phase will be found to be relatively high under steady state conditions, even when originally a catalyst with a higher alcohol and/or alcoholate component has been applied.

It has been found now, that methanol is a less suitable alcohol component than an optimally selected one as far as the reaction is concerned with reference to reaction rates, mass transfer, gas solubilization etc.

Moreover, at high methanol concentrations methylformate will inevitably be formed in competition with other formates.

Since methylformate is relatively volatile, it will be a substantial by-product of the methanol produced unless the steady state formate concentration can be kept deliberately low, which is not inducive to a high hydrogenation rate. Possible methylformate as by-product can be reconverted into methanol.

The hereinbefore described embodiment may be more particularly be carried out in a reaction equipment according to the FIG. 1.

One of the individually produced gas mixtures relatively rich in CO is introduced in the left reactor where carbonylation is the predominant reaction. The carbonylation rate as well as equilibrium are favoured by the relatively high CO partial pressure (i.e. more than in a stoichiometric mixture usually applied).

The ester hydrogenation step (b) may predominantly take place in the right hand reactor. Herein the reaction rate benefits from the high hydrogen partial pressure and the relatively low CO pressure.

At a substantial conversion of the low $H_2/CO$ gas in the left reactor, there will be a net formate production with a $H_2/CO$ consumption ratio less than 2. In the right reactor, substantial conversion of the high $H_2/CO$ gas implies a net consumption of formate. Formate production and consumption may accurately balanced by control of the circulation of liquid catalyst system.

Figure 2:
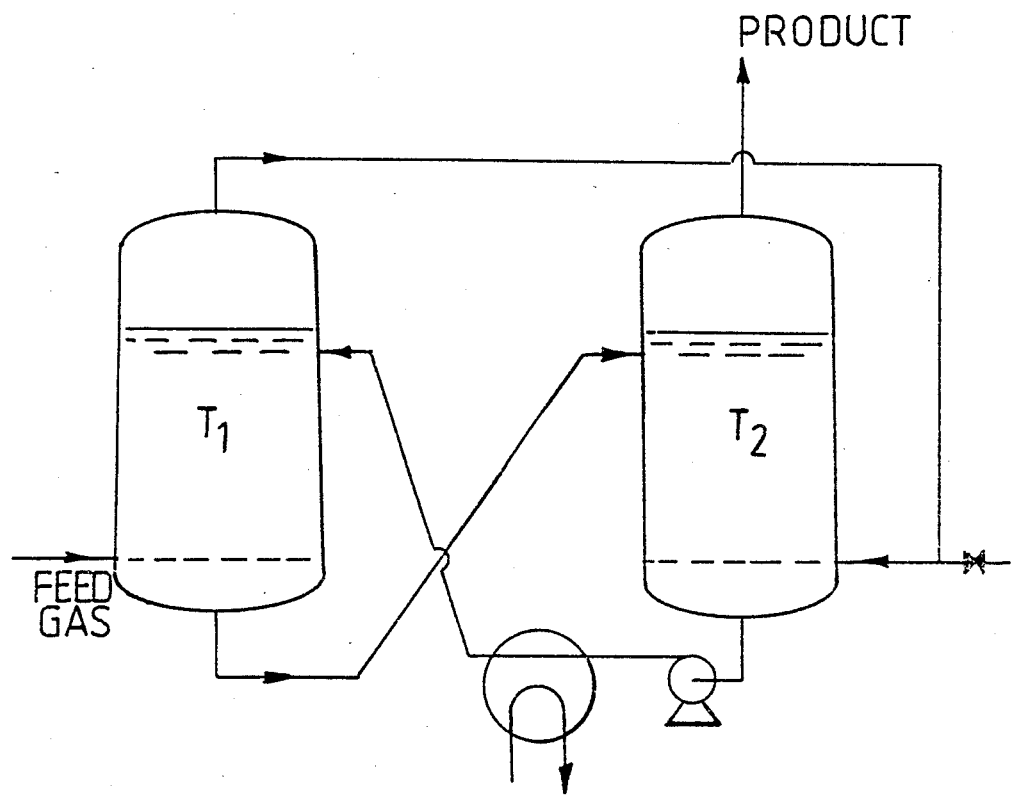
FIG. 2 illustrates a more preferred embodiment wherein the first (carbonylation) reactor is operated at a lower temperature than the second (hydrogenation) reactor.

According to a more preferred embodiment the carbonylation reaction step is carried out at relatively low temperature (from 30°–70° C.) in the left reactor, taking into account that this reaction step is a fast but equilibrium limited reaction, while the second hydrogenation reaction step is carried out at relatively higher temperature (from 70°–120° C.) in the right hand reactor (reference is made to the FIG. 2), taking into account that the ester hydrogenation is not limited by equilibrium but by kinetics. Such a temperature difference as indicated hereinbefore, will be reached automatically, if the total reaction heat is removed from the circulating liquid catalyst system.

It will be appreciated that the before described embodiment offers a greater degree of flexibility than a single stage process, which leads to an overall better performance, e.g. a lower total reactor volume, while also the problem of methanol build up and by-product methyl formate will be minimized.

Moreover, this embodiment can certainly not be regarded as obvious to a skilled person who might only be inclined to look for improved single stage processes, due to the general conception that separate reaction vessels would mean a disadvantage.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following examples further illustrate the invention, without however restricting the scope thereof to these particular embodiments.

All experiments were carried out in a 300 ml magnetically stirred Hastelloy C (Hastelloy is a trade name)

autoclave. The reaction mixtures obtained were analyzed by means of gas-liquid chromatography.

Nickel formate was used which had been preheated under vacuum at 150° C. during 16 hours.

EXAMPLE 1

The autoclave was charged under a nitrogen atmosphere with diglyme (50 ml), nickel formate (10 mmol) and tert-amyl alcohol (20 mmol), heated to a temperature of 45° C. with stirring and kept at this temperature for 0.5 h.

Then, consecutively, tert-amyl alcohol (50 ml) and potassium tert-butylate (50 mmol) were introduced into the autoclave and the autoclave was sealed.

A mixture of a volume ratio of carbon monoxide and hydrogen of 1:2 was introduced into the autoclave until a pressure of 45 bar was obtained.

The autoclave was further heated to a temperature of 80° C. and the pressure was kept at a value between 30 and 60 bar by intermittent introduction of additional carbon monoxide and hydrogen up to pressure increases of 8 bar and 24 bar, of 7 bar and 21 bar, of 6 bar and 18 bar, and of 6 bar and 18 bar respectively after 1 hour, 1.75 h, 2.25 h and 3 h respectively from the start of the reaction.

After a total reaction time of 5 hours, the autoclave was allowed to adopt ambient temperature and then depressurized. The reaction mixture contained a yellow solid substance and 8.1 g methanol and a trace of methyl formate were found.

EXAMPLE 2

In about the same way as described under example 1 an experiment was carried out, with the difference that 10 mmol nickel formate and 50 ml tert-amyl alcohol were introduced in the autoclave.

After 0.5 h at 45° C. under nitrogen, 50 ml tert-amyl alcohol and 50 mmol potassium tert-butylate were added. During the reaction, additional amounts of carbon monoxide and hydrogen were added after 2 h and 3.5 h from the start of the reaction (18 bar pressure increase hydrogen and 6 bar carbon monoxide and 24 bar hydrogen and 8 bar carbon monoxide respectively).

The reaction mixture was kept at 80° C. during the first two hours and at 100° C. during the three subsequent hours. After termination of the reaction 5.4 g methanol was found.

EXAMPLE 3

In about the same way as described under example 1 an experiment was carried out, with the difference that instead of tert-amyl alcohol, isoamyl alcohol was used (20 mmol and 50 ml respectively). While the total pressure was maintained at 47 bar by constant addition of hydrogen and carbon monoxide in a 2:1 ratio. The reaction was terminated after 5 hours at 80° C. and 5.5 g methanol and 1.1 g methyl formate had been obtained.

EXAMPLE 4

In about the same way as described under example 1 an experiment was carried out, with the difference that an initial gas intake of 45 bar hydrogen and 15 bar carbon monoxide was applied. The total pressure was maintained at 47 bar by constant addition of hydrogen and carbon monoxide in a 2:1 ratio. After 5 hours 13.4 g methanol and 1.4 g methyl formate had been obtained.

Comparative Example

In the same way as described under example 1 an experiment was carried out with the difference that the autoclave was charged with diglyme (100 ml), nickel formate (10 mmol) and potassium tert-butylate (50 mmol), whereafter carbon monoxide (15 bar pressure increase) and hydrogen (30 bar pressure increase) were added. The reaction mixture was kept at 80° C. for two hours and at 100° C. for five hours. 1.9 g methanol and 0.2 g methyl formate had been obtained.

Comparison of the latter (obtained according to the process of published Japanese application 56-169,634) results with those obtained in Examples 1–4, clearly show a significant improvement.

EXAMPLE 5

In about the same way as described in example 1, an experiment was carried out, with the difference that after activation under nitrogen during 0.5 h at 45° C. 10 ml tert-amylalcohol and 40 ml diglyme (instead of 50 ml tert-amylalcohol) were introduced into the autoclave.

A mixture of carbon monoxide and hydrogen of a 1:2 ratio was introduced until a pressure of 45 bar and this total pressure was maintained during the further reaction by constant addition of carbon monoxide and hydrogen in a 1:2 ratio.

After a total reaction time of 5 hours at 90° C. 15 g methanol and 3.6 g methyl formate had been obtained.

EXAMPLE 6

In about the same way as described in example 1, an experiment was carried out, with the difference that after activation, 45 ml diglyme and 3.2 g methanol were introduced into the autoclave (instead of 50 ml tert-amylalcohol).

By addition of a hydrogen-carbon monoxide 2:1 ratio mixture, a total pressure of 45 bar was maintained by constant addition of this gas mixture. After a total reaction time of 5 hours at 80° C., 11.6 g methanol and 3.5 g methyl formate were present in the reaction mixture.

We claim:

1. A process for the production of methanol comprising contacting a gaseous mixture of carbon monoxide and hydrogen with a catalytic system in the liquid phase, obtainable by the reaction of:
   component (a): a salt containing a cation of an element of Group VIII of the Periodic Table of Elements,
   component (b): an alcohol, and
   component (c): an alcoholate derived from an alkali metal or from an alkaline earth metal, and
wherein said catalytic system is activated before use by heating at least components (a) and (b) to a temperature of from about 20°–60° C. under a nitrogen atmosphere for 0.3 to 1 hour.

2. The process as claimed in claim 1, characterized in that after this activation, additional amounts of alcohol and alcoholate are added.

3. The process as claimed in claim 1, characterized in that as component (a) a nickel, palladium or cobalt salt is used.

4. The process as claimed in claim 3, characterized in that as component (a) a nickel salt is used.

5. The process as claimed in claim 4, characterized in that nickel formate, nickel acetate, nickel oxalate or nickel tosylate is used.

6. The process as claimed in claim 1, characterized in that as component (b) an alkanol containing 4–20 carbon atoms is used.

7. The process as claimed in claim 6, characterized in that tert-butylalcohol or tert-amylalcohol or mixtures thereof are used.

8. The process as claimed in claim 1, characterized in that as component (c) sodium or potassium alkoxides are used.

9. The process according to claim 8, characterized in that potassium tert-butoxide is used.

10. The process as claimed in claim 1, characterized in that it is carried out in the range of from 30° C. to 120° C.

11. The process as claimed in claim 10, characterized in that it is carried out at a pressure in the range of from 5 to 100 bar.

12. The process as claimed in claim 1, characterized in that it is carried out in an organic diluent.

13. The process as claimed in claim 12, characterized in that a weight ratio of organic diluent and component (a) in the range of from 0.1 to 5000 is used.

14. The process as claimed in claim 12, characterized in that ethers are used as diluent.

15. The process as claimed in claim 14, characterized in that diglyme is used as diluent.

16. The process a claimed in claim 1, characterized in that the mole ratio between components (a) and (b) is in the range of from 1:0.2 to 1:20.

17. The process as claimed in claim 16, characterized in that the mole ratio between components (a) and (b) is in the range of from 1:3 to 1:8.

* * * * *